United States Patent
Ohta et al.

(10) Patent No.: US 8,288,730 B2
(45) Date of Patent: Oct. 16, 2012

(54) PORTABLE RADIOGRAPHIC IMAGE CAPTURING DEVICE

(75) Inventors: Yasunori Ohta, Kanagawa (JP);
Naoyuki Nishino, Kanagawa (JP);
Naoto Iwakiri, Kanagawa (JP); Futoshi Yoshida, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 24 days.

(21) Appl. No.: 12/891,827

(22) Filed: Sep. 28, 2010

(65) Prior Publication Data
US 2011/0073768 A1    Mar. 31, 2011

(30) Foreign Application Priority Data

Sep. 30, 2009  (JP) ................................. 2009-227392

(51) Int. Cl.
*G01T 1/24*    (2006.01)

(52) U.S. Cl. .................................................. 250/370.08

(58) Field of Classification Search .............. 250/370.08
See application file for complete search history.

(56) References Cited

U.S. PATENT DOCUMENTS

| 7,180,110 B2 * | 2/2007 | Komatsu et al. .............. 257/291 |
| 2006/0054822 A1 * | 3/2006 | Tsuchino ................... 250/336.1 |
| 2006/0097177 A1 * | 5/2006 | Yamamoto ............... 250/370.08 |

FOREIGN PATENT DOCUMENTS

| JP | 2000010220 A | * | 1/2000 |
| JP | 2002-311526 A |   | 10/2002 |
| JP | 2009-32854 A  |   | 2/2009 |
| JP | 2009-80103 A  |   | 4/2009 |

* cited by examiner

*Primary Examiner* — Christine Sung
(74) *Attorney, Agent, or Firm* — SOLARIS Intellectual Property Group, PLLC

(57) ABSTRACT

A portable radiographic image capturing device includes an image capturing unit, a control unit, and a connecting member. The image capturing unit is formed in the shape of a flat plate, captures a radiographic, and includes a radiation detector that outputs electric signals expressing a captured radiographic image, the image capturing unit being able to capture a radiographic image from either an obverse side or a reverse side of the flat plate. The control unit includes a controller that controls image capturing operations of the radiation detector. The connecting member connects the image capturing unit and the control unit such that both units can be opened and closed between an unfolded state, in which the both units are lined-up next to one another, and a housed state, in which the both units are folded-up so as to be superposed one on another.

10 Claims, 15 Drawing Sheets

PORTABLE RADIOGRAPHIC IMAGE CAPTURING DEVICE

CROSS-REFERENCE TO RELATED APPLICATION

This application claims priority under 35 USC 119 from Japanese Patent Application No. 2009-227392 filed on Sep. 30, 2009, and is also based on Japanese Patent Application No. 2010-187583 filed on Aug. 24, 2010. The disclosures of these applications are incorporated by reference herein.

BACKGROUND OF THE INVENTION

1. Field of the Invention

The present invention relates to a portable radiographic image capturing device that captures a radiographic image expressed by irradiated radiation.

2. Related Art

Radiation detectors such as Flat Panel Detectors (FPDs), in which a radiation-sensitive layer is disposed on a Thin Film Transistor (TFT) active matrix substrate and that detect irradiated radiation such as X-rays or the like and output electric signals expressing the radiographic image expressed by the detected radiation, and the like have been put into practice in recent years. As compared with a conventional imaging plate, a radiation detector has the advantages that images can be confirmed immediately, and even video images can be confirmed.

Portable radiographic image capturing devices (hereinafter also called electronic cassettes), that incorporate a radiation detector therein and store radiographic image data outputted from the radiation detector, also are being put into practice. Because the electronic cassette has excellent portability, images of a patient can be captured while the patient lies as is on a stretcher or a bed, and it is also easy to adjust the region to be captured by changing the position of the electronic cassette. Therefore, even situations in which images of a patient who cannot move are captured can be dealt with flexibly.

It is generally known that the electrical characteristics of a radiation detector change due to a rise in temperature. Further, heat dissipation and cooling are extremely important in order to improve normal operation and durability of the electric parts.

In Japanese Patent Application Laid-Open (JP-A) No. 2009-80103, the inventors disclose a technique of structuring an electronic cassette such that electronic parts that generate heat and a radiation detector can be separated. In this technique, the electronic cassette is structured by a cassette main body that incorporates a radiation detector therein, and a control unit that is freely detachable from and can be separated from the cassette main body, and that supplies power to the radiation detector, and that controls the radiation detector and receives image information.

JP-A No. 2002-311526 discloses a technique in which a portion of a casing of an electronic cassette can be opened and closed, and a unit part, that includes a radiation detector and that is made into a unit, is structured so as to be removable.

By using the technique disclosed in JP-A No. 2009-80103, the control unit is structured so as to be able to be separated from the cassette main body. By using the technique disclosed in JP-A No. 2002-311526, a portion of the casing of the electronic cassette can be opened and closed, and the unit part is structured so as to be removable. The section that generates heat can thereby be separated from the radiation detector.

However, in these techniques, because a portion must be physically separated, the operability is poor. Further, these techniques are not techniques that improve the heat dissipating and cooling efficiency of the electronic cassette itself.

SUMMARY

In view of the above-described circumstances, the present invention provides a portable radiographic image capturing device that improves the cooling effect while suppressing a deterioration in operability.

An aspect of the present invention is a portable radiographic image capturing device having: an image capturing unit that is formed in the shape of a flat plate, and captures a radiographic image expressed by irradiated radiation, and has a radiation detector that outputs electric signals expressing a captured radiographic image, the image capturing unit being able to capture a radiographic image by radiation irradiated from either an obverse side or a reverse side of the flat plate; a control unit having a controller that controls image capturing operations of the radiation detector; and a connecting member that connects the image capturing unit and the control unit such that the image capturing unit and the control unit can be opened and closed between an unfolded state, in which the image capturing unit and the control unit are lined-up next to one another, and a housed state, in which the image capturing unit and the control unit are folded-up so as to be superposed one on another.

In accordance with this aspect, the image capturing unit and the control unit are connected by the connecting member so as to be able to open and close between the unfolded state and the housed state. Therefore, deterioration in the operability at the time of setting the image capturing unit and the control unit in the unfolded state in order to physically separate them is suppressed. Further, the cooling effect can be improved by setting the image capturing unit and the control unit in the unfolded state.

In the present aspect, the portable radiographic image capturing device may further have a detecting section that detects an opened/closed state of the image capturing unit and the control unit, wherein, on the basis of results of detection by the detecting section, the controller may control the portable radiographic image capturing device to carry out still image capturing if the opened/closed state of the image capturing unit and the control unit is the housed state, and may control the portable radiographic image capturing device to carry out video image capturing if the opened/closed state is the unfolded state.

In the present aspect, the portable radiographic image capturing device may further have an accepting section that accepts an image capturing instruction for still image capturing also if the opened/closed state of the image capturing unit and the control unit is the unfolded state, wherein, if the accepting section accepts an image capturing instruction for still image capturing, the controller may control the portable radiographic image capturing device to carry out still image capturing also in the unfolded state.

In the present aspect, at the radiation detector, a charge generating layer, at which charges are generated due to radiation being irradiated, and a substrate, that accumulates the charges generated at the charge generating layer and at which are formed switch elements for reading-out the charges, may be layered, and the radiation detector may be incorporated within the image capturing unit such that, in the housed state, the charge generating layer is at a surface side that opposes the control unit.

The radiation detector may include a substrate and a conversion layer that converts radiation irradiated onto the substrate into light, and the charges may be generated at the charge generating layer due to the light converted from the radiation at the conversion layer.

The charge generating layer may include an organic photoelectric conversion material.

The radiation detector may be formed at a substrate that contains plastic resin, aramid, bio-nanofibers, or flexible glass.

In the present aspect, the connecting member may contain therein an amplifying circuit that amplifies the electric signals outputted from the radiation detector.

In the present aspect, the control unit may include a radio communication section that carries out radio communication with an external device.

In the present aspect, a surface of the control unit may be formed to have convex and concave shapes.

In the present aspect, the control unit may have a display section at a surface that opposes the image capturing unit in the housed state.

Thus, the radiographic image capturing device of the present aspect can improve the cooling effect while suppressing a deterioration in operability.

BRIEF DESCRIPTION OF THE DRAWINGS

Exemplary embodiments of the present invention will be described in detail based on the following figures, wherein.

DETAILED DESCRIPTION

Figure 1:
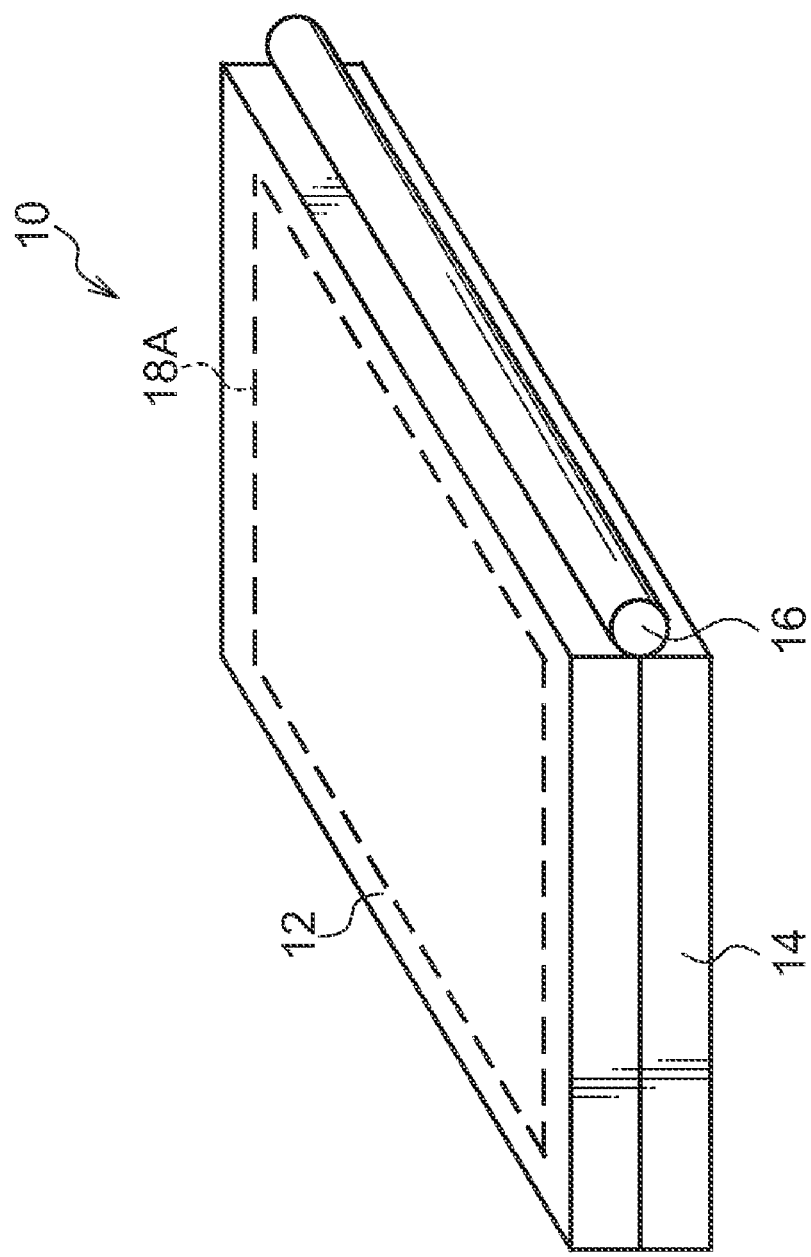
FIG. 1 is a perspective view showing the structure of an electronic cassette in a housed state relating to an exemplary embodiment.
Figure 2:
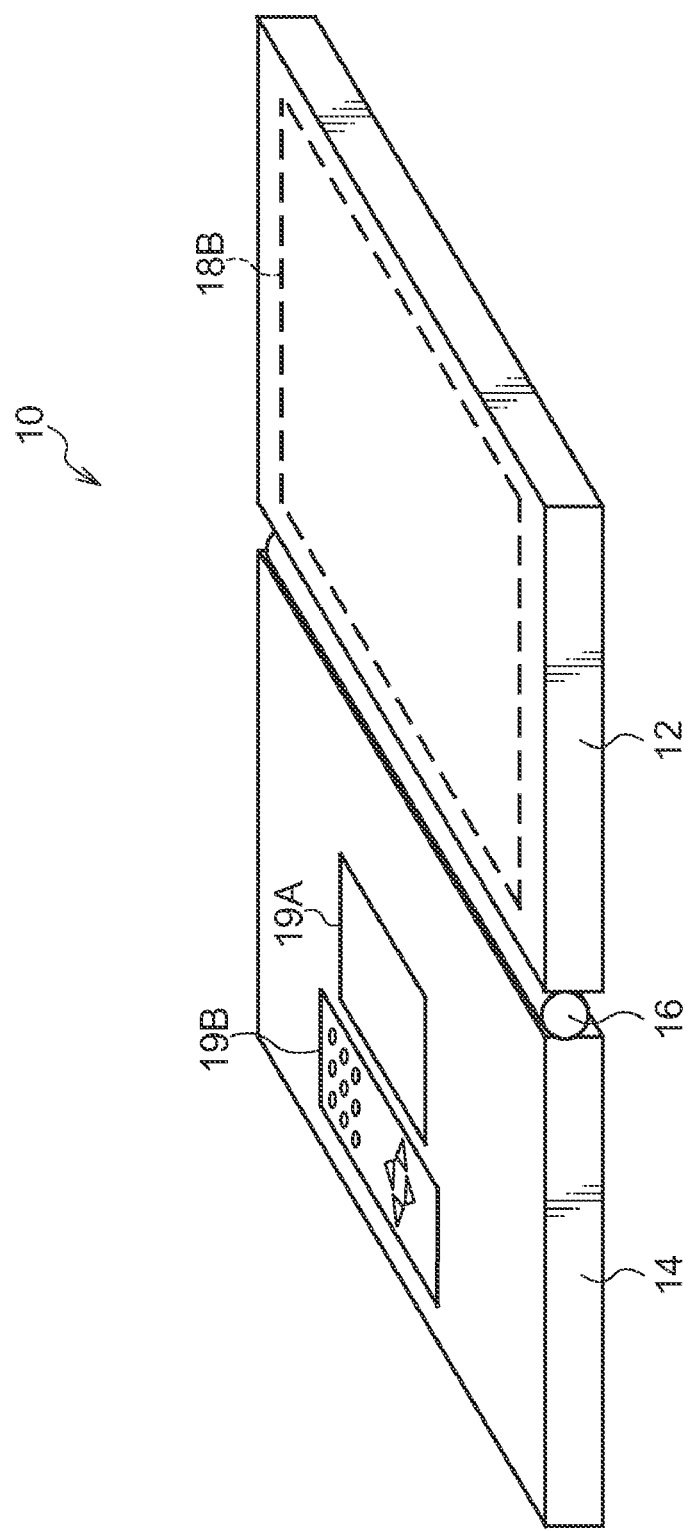
FIG. 2 is a perspective view showing the structure of the electronic cassette in an unfolded state relating to the exemplary embodiment.

Perspective views showing the structure of an electronic cassette 10 relating to an exemplary embodiment are shown in FIG. 1 and FIG. 2.

As shown in FIG. 1, at the electronic cassette 10, an image capturing unit 12 and a control unit 14 are connected by a hinge 16 so as to be able to open and close. The image capturing unit 12 is shaped as a flat plate, and incorporates a radiation detector 20 (see FIG. 3) therein, and captures a radiographic image by irradiated radiation. The control unit 14 incorporates therein a controller 50 that controls the image capturing operations of the radiation detector 20.

Due to one of the image capturing unit 12 and the control unit 14 being rotated around the hinge 16 with respect to the other, the image capturing unit 12 and the control unit 14 can be opened and closed between an unfolded state (FIG. 2) in which the image capturing unit 12 and the control unit 14 are lined-up next to one another, and a housed state (FIG. 1) in which the image capturing unit 12 and the control unit 14 are folded-up so as to be superposed one on another.

In the present exemplary embodiment, the image capturing unit 12 and the control unit 14 are made to be the same height in order to eliminate a step between the image capturing unit 12 and the control unit 14 in the unfolded state (FIG. 2).

A display section 19A and an operation panel 19B are provided at the surface of the control unit 14 which surface faces the image capturing unit 12 in the housed state. The display section 19A has a display device that can display images and the like. The operation panel 19B has various types of buttons such as a cross key, a ten key, and the like.

Figure 3:
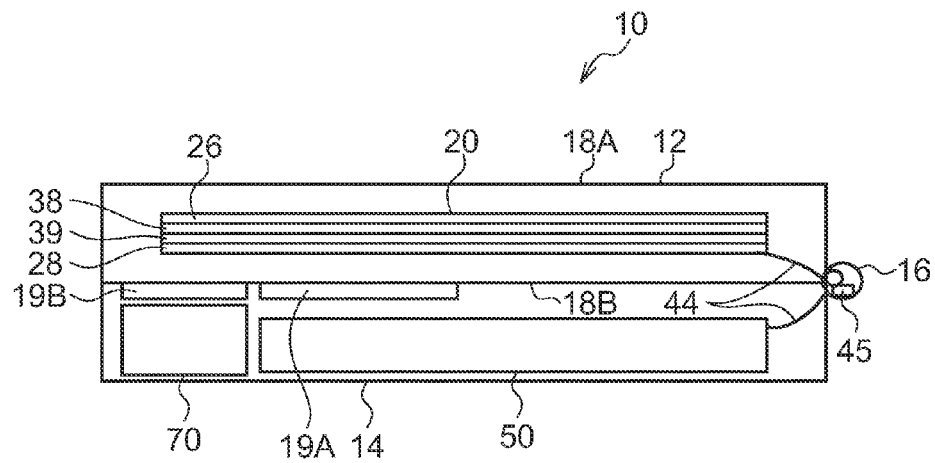
FIG. 3 is a sectional view showing the schematic structure of the electronic cassette in the housed state.

A sectional view showing the schematic structure of the electronic cassette 10 is shown in FIG. 3.

The radiation detector 20, that captures a radiographic image expressed by irradiated radiation and outputs electric signals expressing the captured radiographic image, is incorporated in the image capturing unit 12.

The controller 50 that controls the image capturing operations of the radiation detector, and a power source section 70 that supplies electric power to the controller 50, are incorporated in the control unit 14.

The radiation detector 20 and the controller 50 are connected by a connection wire 44 that is provided via the hinge 16.

An opening/closing sensor 45, that detects the opened/closed state of the image capturing unit 12 and the control unit 14, is provided at the hinge 16. The opening/closing sensor 45 may detect the opened/closed state by detecting a change in the magnetic field due to the opening or closing of the image capturing unit 12 and the control unit 14 by combining, for example, a small-sized magnet and a Hall sensor. Or, the opening/closing sensor 45 may be an angle sensor that detects the angle of the opening/closing, or may be plural mechanical switches that are disposed such that combinations of the on and off states change in accordance with the open/closed state.

Figure 4:
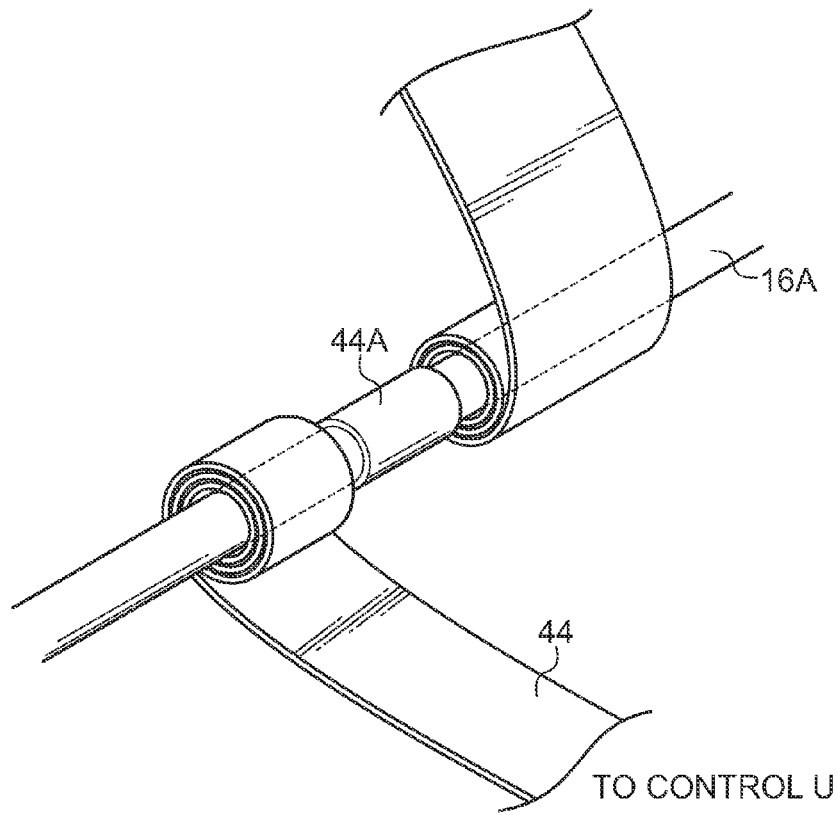
FIG. 4 is a perspective view showing the structure of a connection wire within a hinge relating to the exemplary embodiment.

Because the image capturing unit 12 and the control unit 14 can be opened and closed by the hinge 16, bending or bending stress is constantly applied to the hinge 16 portion of the connection wire 44, and it is easy for disconnection or breakage to arise. Therefore, in the present exemplary embodiment, the connection wire 44 is formed by, for example, a flexible printed substrate or the like. As shown in FIG. 4, the connection wire 44 is wound plural times around a rotation shaft 16A of the hinge 16, that supports the image capturing unit 12 and the control unit 14 such that they can be opened and closed, so as to form a cylindrical tube portion 44A. Tape is wound on the outer periphery thereof so as to hold and fix the cylindrical tube portion 44A. Further, the both sides of the cylindrical tube portion 44A of the connection wire 44 are respectively wound plural times around the rotation shaft 16A spirally and with leeway, and are led-out to the image capturing unit 12 and the control unit 14 respectively.

Due thereto, in a case in which the image capturing unit 12 is opened or closed, the connection wire 44 rotates along the rotation shaft 16A. Because the both sides of the cylindrical tube portion 44A of the connection wire 44 are respectively wound with leeway around the rotation shaft 16A, the connection wire 44 very flexibly follows the opening or closing of the image capturing unit 12, and the connection wire 44 does not break.

Figure 5:
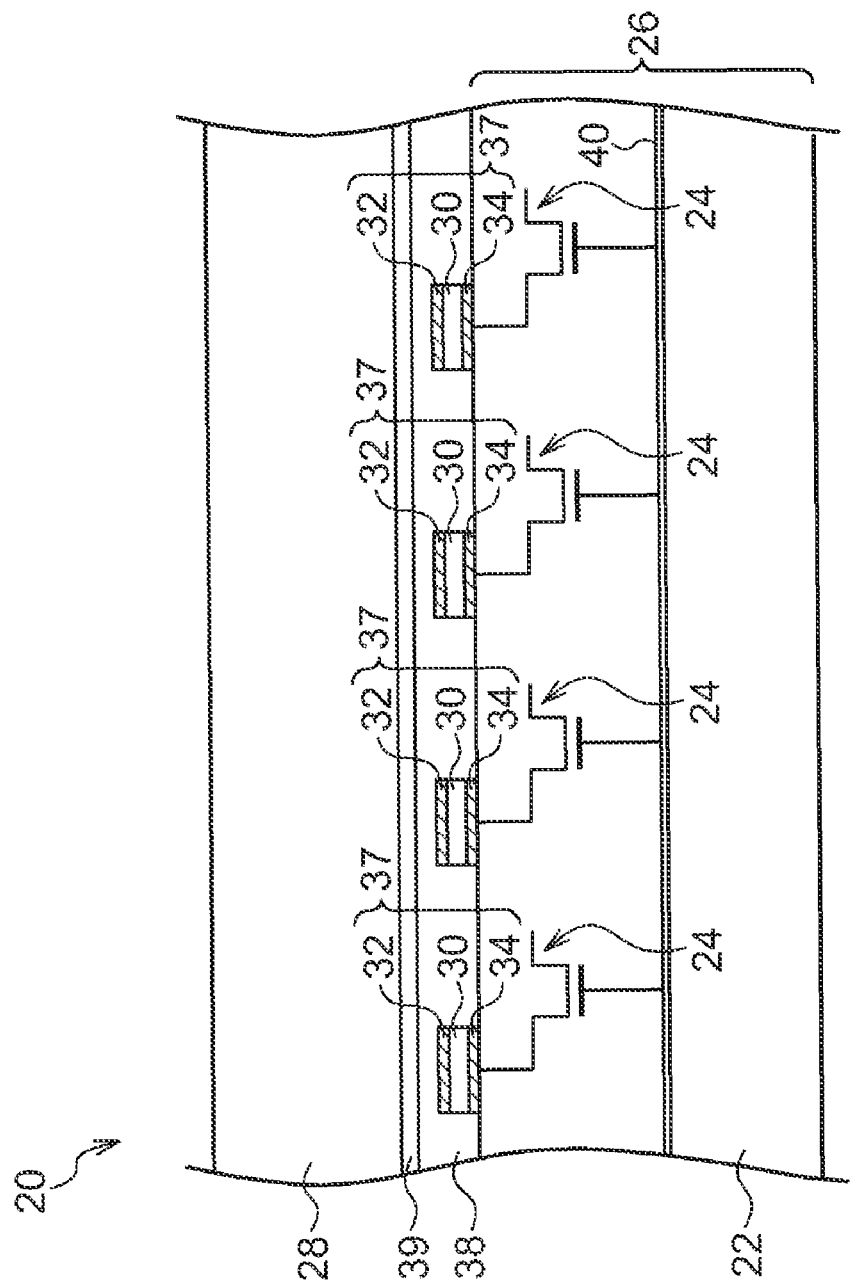
FIG. 5 is a sectional view schematically showing the structure of a radiation detector relating to the exemplary embodiment.
Figure 6:
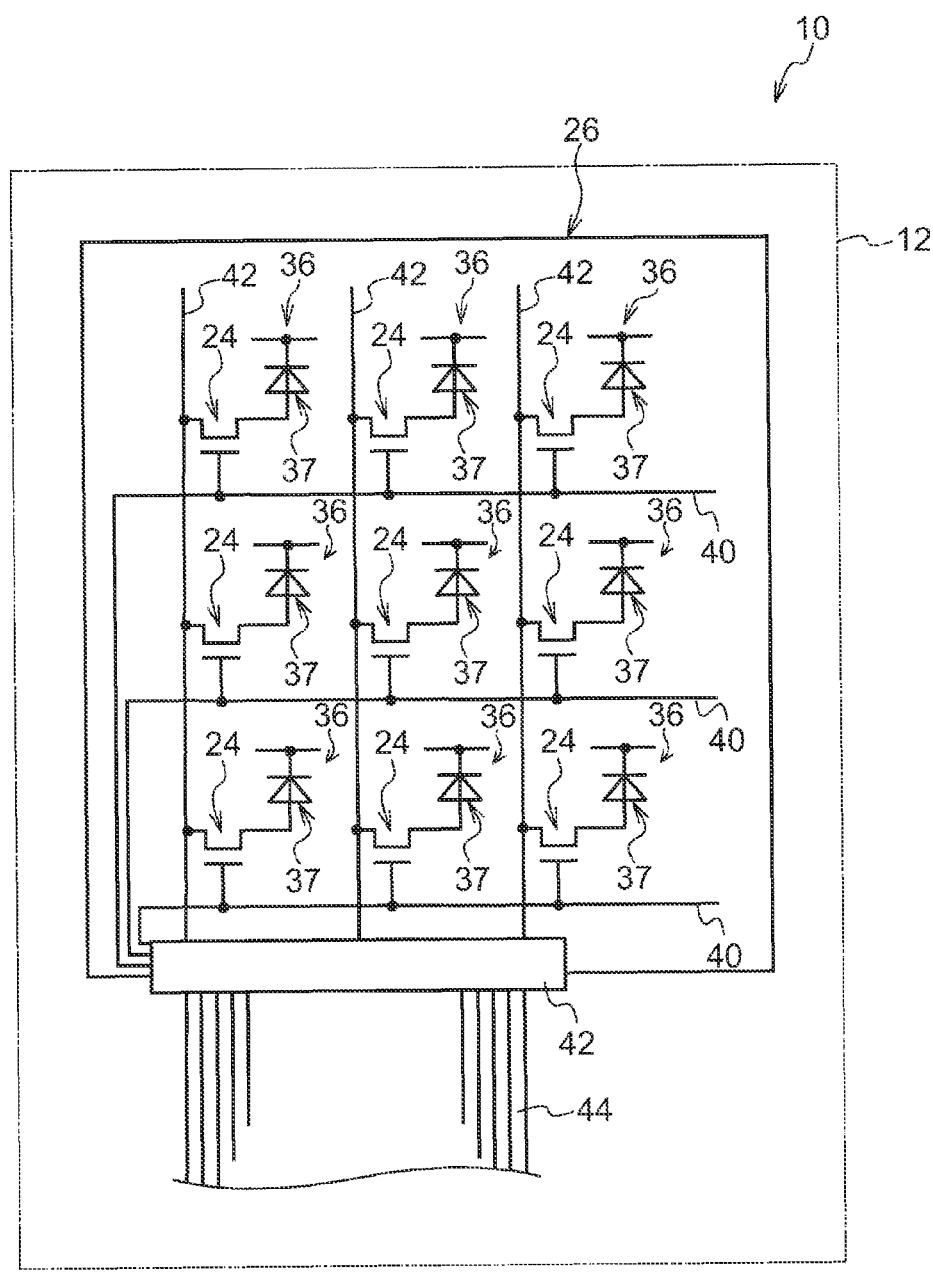
FIG. 6 is a plan view showing the structure of the radiation detector relating to the exemplary embodiment.

The radiation detector 20 relating to the present exemplary embodiment is described next with reference to FIG. 5 and FIG. 6. FIG. 5 is a sectional view schematically showing the structure of the radiation detector 20 relating to the present exemplary embodiment. FIG. 6 is a plan view showing the structure of the radiation detector 20.

As shown in FIG. 5, the radiation detector 20 has a TFT substrate 26 at which switch elements 24 such as thin film transistors (TFTs) or the like are formed on an insulating substrate 22.

A scintillator layer 28, that converts incident radiation into light, is formed on the TFT substrate 26 as an example of a radiation converting layer that converts incident radiation.

For example, CsI:Tl or GOS ($Gd_2O_2S$:Tb) can be used as the scintillator layer 28. Note that the scintillator layer 28 is not limited to these materials.

For example, a glass substrate, any of various types of ceramic substrates, or a resin substrate can be used as the insulating substrate 22. Note that the insulating substrate 22 is not limited to these materials.

Photoconductive layers 30, that generate charges due to the light converted by the scintillator layer 28 being incident thereon, are disposed between the scintillator layer 28 and the TFT substrate 26. Bias electrodes 32 for applying bias voltage to the photoconductive layers 30 are formed on the scintillator layer 28 side surfaces of the photoconductive layers 30.

The photoconductive layer 30 includes an organic photoelectric conversion material, absorbs light that is emitted from the scintillator layer 28, and generates charges that correspond to the absorbed light. The photoconductive layer 30, that includes an organic photoelectric conversion material in this way, has a sharp absorption spectrum in the visible range, and there is hardly any absorption by the photoconductive layer 30 of electromagnetic waves other than the light emitted by the scintillator 28, and noise, that is generated by radiation such as X-rays or the like being absorbed at the photoconductive layer 30, can be effectively suppressed.

In order to most efficiently absorb the light that is emitted at the scintillator layer 28, it is preferable that the absorption peak wavelength of the organic photoelectric conversion material that structures the photoconductive layer 30 be nearer to the emission peak wavelength of the scintillator layer 28. It is ideal that the absorption peak wavelength of the organic photoelectric conversion material and the emission peak wavelength of the scintillator layer 28 coincide, but if the difference therebetween is small, the light emitted from the scintillator layer 28 can be absorbed sufficiently. Specifically, it is preferable that the difference between the absorption peak wavelength of the organic photoelectric conversion material and the emission peak wavelength, with respect to radiation, of the scintillator layer 28 be within 10 nm, and it is more preferable for the difference to be within 5 nm.

Examples of organic photoelectric conversion materials that can satisfy such a condition are, for example, quinacridone organic compounds and phthalocyanine organic compounds. For example, the absorption peak wavelength in the visible range of quinacridone is 560 nm. Therefore, if quinacridone is used as the organic photoelectric conversion material and CsI(Tl) is used as the material of the scintillator layer 28, the difference in the peak wavelengths can be made to be within 5 nm, and the amount of charges generated at the photoconductive layer 30 can be made to be substantially the maximum.

Charge collecting electrodes 34, that collect the charges generated at the photoconductive layers 30, are formed at the TFT substrate 26. At the TFT substrate 26, the charges collected at the respective charge collecting electrodes 34 are read-out by the switch elements 24.

As shown in FIG. 6, the charge collecting electrodes 34 are disposed in a two-dimensional form on the TFT substrate 26. In correspondence therewith, the switch elements 24 are disposed in a two-dimensional form at the insulating substrate 22.

Plural gate lines 40 that extend in a given direction (the row direction) and are for turning the respective switch elements 24 on and off, and plural data lines 42 that extend in a direction (the column direction) orthogonal to the gate lines 40 and are for reading-out the charges via the switch elements 24 that are in on states, are provided at the TFT substrate 26.

A smoothing layer 38 for smoothing the top of the TFT substrate 26 is provided on the TFT substrate 26. Further, an adhesive layer 39 for adhering the scintillator layer 28 to the TFT substrate 26, is formed on the smoothing layer 38 between the TFT substrate 26 and the scintillator layer 28.

Sensor portions 37 that structure respective pixel portions 36 at the radiation detector 20 can be structured by a bias electrode 32 and a charge collecting electrode 34 that form a pair, and an organic layer that contains the organic photoconductive layer 30 that is sandwiched between the bias electrode 32 and the charge collecting electrode 34. More specifically, this organic layer can be formed by the stacking of or the combining of a region that absorbs electromagnetic waves, a photoelectric conversion region, an electron transport region, a hole transport region, an electron blocking region, a hole blocking region, a crystallization preventing region, electrodes, an interlayer contact improving region, and the like.

It is preferable that the organic layer contain an organic p-type compound or an organic n-type compounds.

An organic p-type semiconductor (compound) is a donor organic semiconductor (compound) exemplified mainly by hole-transporting organic compounds, and means an organic compound that has the property that it easily donates electrons. More specifically, an organic p-type semiconductor (compound) means, when two organic materials are used by being made to contact one another, the organic compound whose ionization potential is smaller. Accordingly, any organic compound can be used as the donor organic compound, provided that it is an electron-donating organic compound.

An organic n-type semiconductor (compound) is an accepter organic semiconductor (compound) exemplified mainly by electron-transporting organic compounds, and means an organic compound that has the property that it easily accepts electrons. More specifically, an organic n-type semiconductor (compound) means, when two organic compounds are used by being made to contact one another, the organic compound whose electron affinity is greater. Accordingly, any organic compound can be used as the accepter organic compound, provided that it is an electron-accepting organic compound.

Materials that can be used as the organic p-type semiconductor and the organic n-type semiconductor, and the structure of the photoconductive layer 30, are described in detail in JP-A No. 2009-32854, and therefore, description thereof is omitted.

Figure 7:
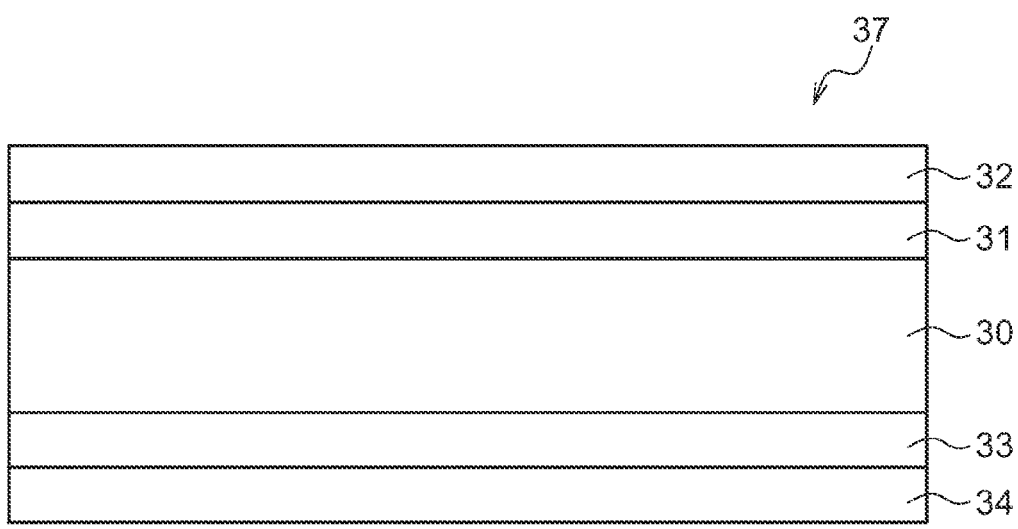
FIG. 7 is a sectional view showing the configuration of a sensor portion relating to the exemplary embodiment.

Here, it suffices for the sensor portion 37 that structures each pixel portion 36 to include at least the charge collecting electrode 34, the photoconductive layer 30 and the bias electrode 32. However, in order to suppress an increase in dark current, as shown in FIG. 7, it is preferable that the sensor portion 37 be provided with at least one of an electron blocking film 33 and a hole blocking film 31, and it is more preferable that the sensor portion 37 be provided with the both.

The electron blocking film 33 can be provided between the charge collecting electrode 34 and the photoconductive layer 30. The electron blocking film 33 can suppress the injection of electrons from the charge collecting electrode 34 into the photoconductive layer 30 and an increase in dark current, when bias voltage is applied between the charge collecting electrode 34 and the bias electrode 32.

An electron-donating organic material can be used for the electron blocking film 33.

It suffices to select the material, that is actually used for the electron blocking film 33, in accordance with the material of the electrode adjacent thereto, the material of the photoconductive layer 30 adjacent thereto, and the like. It is preferable that the material have an electron affinity (Ea) that is 1.3 eV or more greater than the work function (Wf) of the material of the electrode adjacent thereto, and have an ionization potential (Ip) that is equal to or smaller than the ionization potential of the material of the photoconductive layer 30 adjacent thereto. Materials that can be used as this electron-donating organic material are described in detail in JP-A No. 2009-32854, and therefore, description thereof is omitted.

In order to reliably exhibit a dark current suppressing effect and to prevent a decrease in the photoelectric conversion efficiency of the sensor portion 37, it is preferable that the thickness of the electron blocking film 33 be from 10 nm to 200 nm, and more preferable that the thickness be from 30 nm to 150 nm, and particularly preferable that the thickness be from 50 nm to 100 nm.

The hole blocking film 31 can be provided between the photoconductive layer 30 and the bias electrode 32. The hole blocking film 31 can suppress the injecting of holes from the bias electrode 32 into the photoconductive layer 30 and an increase in dark current, when bias voltage is applied between the charge collecting electrode 34 and the bias electrode 32.

An electron-accepting organic material can be used for the hole blocking film 31.

In order to reliably exhibit a dark current suppressing effect and to prevent a decrease in the photoelectric conversion efficiency of the sensor portion 37, it is preferable that the thickness of hole blocking film 31 be from 10 nm to 200 nm, and more preferable that the thickness be from 30 nm to 150 nm, and particularly preferable that the thickness be from 50 nm to 100 nm.

It suffices to select the material, that is actually used for the hole blocking film 31, in accordance with the material of the electrode adjacent thereto, the material of the photoconductive layer 30 adjacent thereto, and the like. It is preferable that the material have an ionization potential (Ip) that is 1.3 eV or more greater than the work function (Wf) of the material of the electrode adjacent thereto, and have an electron affinity (Ea) that is equal to or greater than the electron affinity of the material of the photoconductive layer 30 adjacent thereto. Materials that can be used as this electron-accepting organic material are described in detail in JP-A No. 2009-32854, and therefore, description thereof is omitted.

Figure 8:
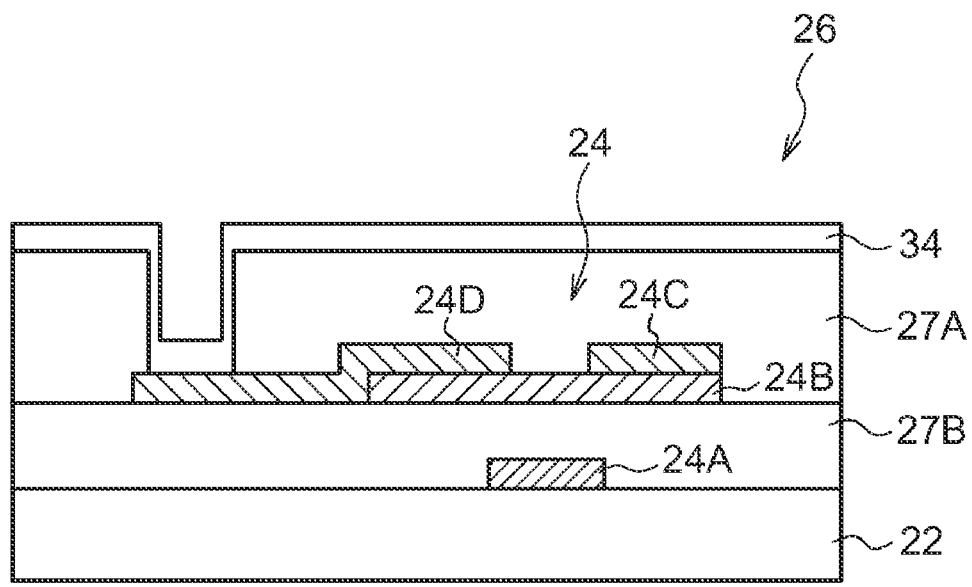
FIG. 8 is a sectional view showing the configuration of a switch element formed on a TFT substrate relating to the exemplary embodiment.

The structure of the switch element 24 that is formed at the TFT substrate 26 relating to the present exemplary embodiment is shown schematically in FIG. 8.

The switch element 24 is formed on the insulating substrate 22 so as to correspond to the charge collecting electrode 34. The region at which the switch element 24 is formed has, in plan view, a portion that is superposed with the charge collecting electrode 34. Due to such a structure, the storage capacitor 68, the switching element 24 and the sensor portion 72 at each pixel portion are superposed in the thickness direction, and the storage capacitor 68, the switch element 24 and the sensor portion 72 can be disposed in a small surface area.

The switching element 24 is electrically connected to the corresponding charge collecting electrode 34, via wiring of an electrically-conductive material that is formed so as to pass-through an insulating film 27A that is provided between the insulating substrate 22 and the charge collecting electrode 34. Due thereto, the charges collected at the charge collecting electrode 34 can be moved to the switch element 24.

At the switch element 24, a gate electrode 24A, a gate insulating film 27B and an active layer (channel layer) 24B are layered, and further, the switch element 24 is structured as a thin-film transistor at which a source electrode 24C and a drain electrode 24D are formed on the active layer 24B with a predetermined interval therebetween. At the radiation detector 20, the active layer 24B is formed of an amorphous oxide. As the amorphous oxide that structures the active layer 24B, oxides containing at least one of In, Ga and Zn (e.g., In—O types) are preferable, oxides containing at least two of In, Ga and Zn (e.g., In—Zn—O types, In—Ga—O types, Ga—Zn—O types) are more preferable, and oxides containing In, Ga and Zn are particularly preferable. As an In—Ga—Zn—O type amorphous oxide, amorphous oxides whose composition in a crystal state is expressed by $InGaO_3(ZnO)_m$ (where m is a natural number of less than 6) are preferable, and in particular, $InGaZnO_4$ is more preferable.

If the active layer 24B of the switch element 24 is formed by an amorphous oxide, radiation such as X-rays and the like is not absorbed, or even if absorbed, the absorbed amount will be extremely small. Therefore, the occurrence of noise at the signal outputting section 14 can be effectively suppressed.

Here, both the amorphous oxide that structures the active layer 24B of the switch element 24 and the organic photoelectric conversion material that structures the above-described photoconductive layer 30 can be formed as films at low temperatures. Accordingly, the insulating substrate 22 is not limited to a highly heat-resistant substrate such as a semiconductor substrate, a quartz substrate, a glass substrate or the like, and a flexible substrate of plastic or the like, and aramid and bio-nanofibers can be used. Specifically, flexible substrates of polyesters such as polyethylene terephthalate, polybutylene phthalate, polyethylene naphthalate and the like, polystyrene, polycarbonate, polyethersulfone, polyarylate, polyimide, polycycloolefin, norbornene resin, poly(chlorotrifluoroethylene), and the like can be used. By using a flexible substrate made of such a plastic, the radiation detector 20 can be made to be lightweight, which is favorable for, for example, carrying the electronic cassette 10, and the like.

Further, an insulating layer for ensuring the insulating ability, a gas barrier layer for preventing the transmission of moisture and oxygen, an undercoat layer for improving the flatness and the adhesiveness with the electrodes and the like may be provided at the insulating substrate 22.

High-temperature processes of 200° or more can be applied to aramid. Therefore, the transparent electrode material can be hardened at a high temperature and made to have low resistance, and further, automatic packaging of a driver IC, including a solder reflow step, also can be handled. Moreover, because the coefficient of thermal expansion of aramid is near to those of ITO (indium tin oxide) and glass substrates, there is little warping after manufacture, and the substrate is difficult to break. In addition, as compared with a glass substrate and the like, a thin substrate can be formed by using aramid. Note that the insulating substrate 22 may be formed by layering an ultra-thin glass substrate and aramid.

Bio-nanofibers are fibers in which a cellulose microfibril bundle (bacteria cellulose) that can produce bacteria (acetic acid bacterium, Acetobacter Xylinum), and a transparent resin are compounded. The cellulose microfibril bundle has a width of 50 nm which is a size of 1/10 with respect to the visible light wavelength, and has high strength, high elasticity, and low thermal expansion. By impregnating and hardening a transparent resin, such as acrylic resin, epoxy resin or the like, in bacteria cellulose, bio-nanofibers that contain up to 60 to 70% fiber while still exhibiting light transmittance of about 90% at a wavelength of 500 nm, are obtained. Bio-nanofibers have a low coefficient of thermal expansion (3 to 7 ppm) that is comparable to that of silicon crystal, have strength (460 MPa) to the same extent as that of steel, have high elasticity (30 GPa), and are flexible. Therefore, the insulating substrate 22 can be formed to be thin as compared with a glass substrate or the like.

The TFT substrate 26 is, as shown in FIG. 6, in plan view, formed in the shape of a quadrilateral having four sides at the outer edge. Specifically, the TFT substrate 26 is rectangular.

A connection terminal 42, to which the individual gate lines 40 and the individual data lines 42 are connected, is disposed at one side at the peripheral end portion of the TFT substrate 26 as seen in plan view.

The connection terminal 42 is connected to the controller 50 via the connection wire 44.

Radiation may be irradiated onto the radiation detector 20 from the obverse side thereof at which the scintillator layer 28 is adhered, or radiation may be irradiated from the TFT substrate 26 side (the reverse side). At the radiation detector 20, in a case in which radiation is irradiated from the obverse side, light is emitted more strongly at the top surface side (the side opposite the TFT substrate 26) of the scintillator layer 28. In a case in which radiation is irradiated from the reverse side, radiation that is transmitted through the TFT substrate 26 is incident on the scintillator layer 28, and the TFT substrate 26 side of the scintillator layer 28 emits light more strongly. Charges are generated at the respective photoconductive layers 30 due to the light that is generated at the scintillator layer 28. Therefore, at the radiation detector 20, in the case in which radiation is irradiated from the obverse side, the radiation is not transmitted through the TFT substrate 26. Therefore, the sensitivity to radiation can be designed to be higher in the case in which radiation is irradiated from the obverse side than in the case in which radiation is irradiated from the reverse side. Further, in the case in which radiation is irradiated from the reverse side, the light-emitting positions of the scintillator layer 28 with respect to the respective photoconductive layers 30 are closer than in the case in which radiation is irradiated from the obverse side. Therefore, the resolution of the radiographic image obtained by image capturing is higher in the case in which radiation is irradiated from the reverse side.

The radiation detector 20 is incorporated in the image capturing unit 12 such that, in the housed state as shown in FIG. 3, the scintillator layer 28 is at the control unit 14 side and the TFT substrate 26 is at the outer side (the side opposite the control unit 14 side). In the housed state, the surface of the image capturing unit 12 that is the outer side is an irradiated surface 18A for reverse irradiation (see FIG. 1) in which radiation is irradiated onto the radiation detector 20 from the reverse side, and the surface facing the control unit 14 is an irradiated surface 18B for obverse irradiation (see FIG. 2) in which radiation is irradiated onto the radiation detector 20 from the obverse side.

Figure 9:
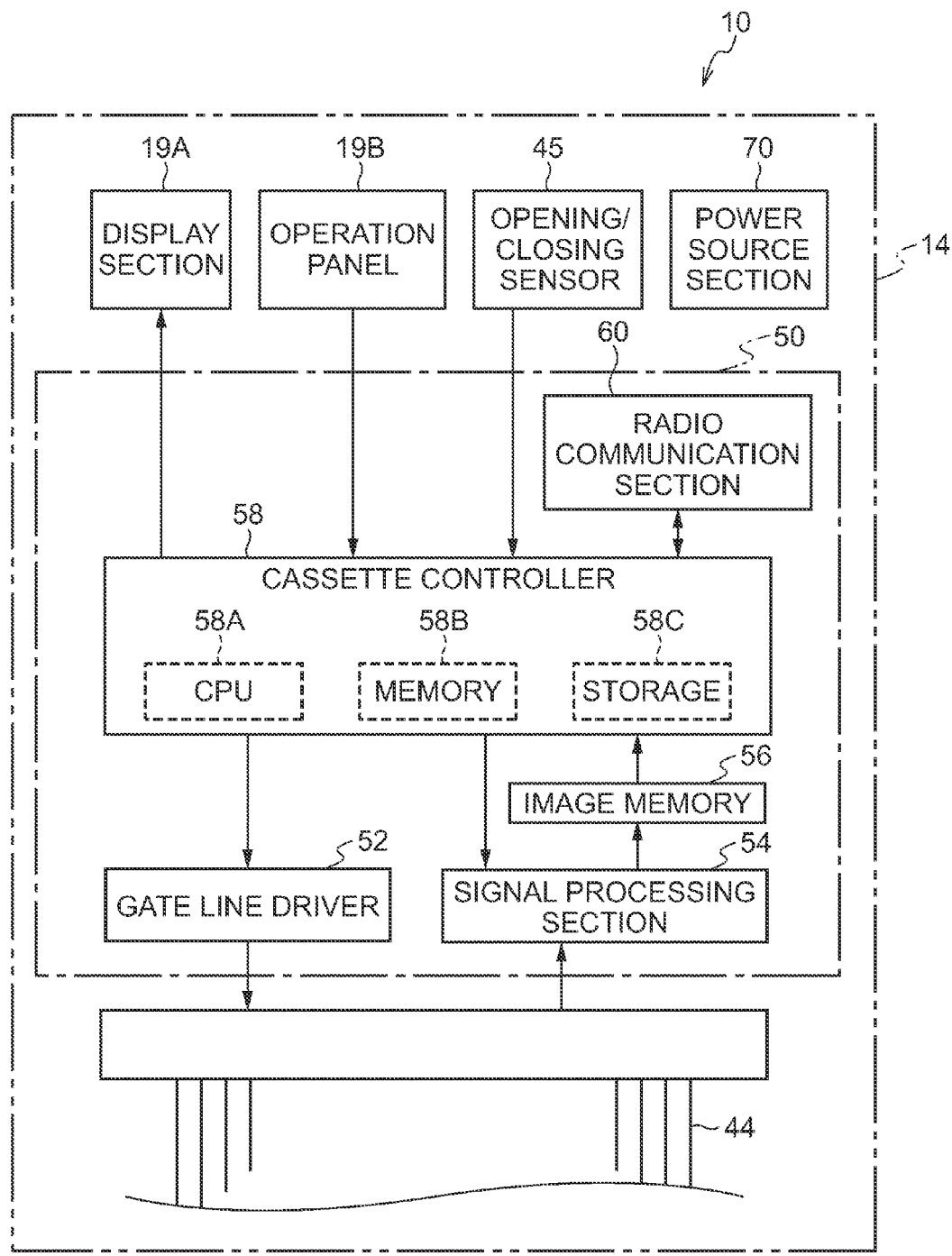
FIG. 9 is a block diagram showing the schematic structure of a controller relating to the exemplary embodiment.

A block diagram showing the schematic structure of the controller 50 relating to the present exemplary embodiment is shown in FIG. 9.

As shown in FIG. 9, the controller 50 has a gate line driver 52, a signal processing section 54, an image memory 56, a cassette controller 58, and a radio communication section 60.

The respective switch elements 24 (see FIG. 5 and FIG. 6) are turned on in order in units of rows by signals that are supplied from the gate line driver 52 via the gate lines 40. The charges read-out by the switch elements 24 that have been turned on are transferred to the data lines 42 as electric signals, and are inputted to the signal processing section 54. Due thereto, the charges are read-out in order in units of rows, and a two-dimensional radiographic image can be acquired.

Although not illustrated, the signal processing section 54 has, for each of the individual data lines 42, an amplifying circuit, that amplifies the inputted electric signal, and a sample/hold circuit. After the electric signals transferred through the individual data lines 42 are amplified at the amplifying circuits, the signals are held in the sample/hold circuits. Further, a multiplexer and an A/D (analog/digital) converter are connected in that order to the output sides of the sample/hold circuits. The electric signals held in the individual sample/hold circuits are inputted in order (serially) to the multiplexer, and are converted into digital image data by the A/D converter.

The image memory 56 is connected to the signal processing section 54. The image data, that is outputted from the A/D converter of the signal processing section 54, is stored in order in the image memory 56. The image memory 56 has a storage capacity that can store a predetermined number of frames of image data. Each time that capturing of a radiographic image is carried out, the image data obtained by the image capturing is successively stored in the image memory 56.

The image memory 56 is connected to the cassette controller 58. The cassette controller 58 is structured by a microcomputer, and has a Central Processing Unit (CPU) 58A, a memory 58B including a ROM and a RAM, and a non-volatile storage 58C formed by a flash memory or the like. The cassette controller 58 controls the operations of the entire electronic cassette 10.

The radio communication section 60 is connected to the cassette controller 58. The radio communication section 60 corresponds to wireless Local Area Network (LAN) standards exemplified by Institute of Electrical and Electronics Engineers (IEEE) 802.11a/b/g or the like. The radio communication section 60 controls the transfer of various types of information to and from external devices by radio communication. The cassette controller 58 can, via the radio communication section 60, communicate by radio with an external device that controls the overall radiographic image capturing such as a console or the like, and can transmit and receive various types of information to and from the console. The cassette controller 58 stores various types of information (data), such as image capturing conditions, patient information, and the like that are received from the console via the radio communication section 60, and starts reading-out of the charges on the basis of the image capturing conditions.

The display section 19A, the operation panel 19B, and the opening/closing sensor 45 are respectively connected to the cassette controller 58. The cassette controller 58 can control the display of various types of information on the display section 19A, and can know of the contents of operation with respect to the operation panel 19B and the opened/closed state of the image capturing unit 12 and the control unit 14.

As mentioned above, the power source section 70 is provided at the electronic cassette 10. The above-described various types of circuits and respective elements (the display section 19A, the operation panel 19B, the opening/closing sensor 45, the gate line driver 52, the signal processing section 54, the image memory 56, the radio communication section 60, and the microcomputer that functions as the cassette controller 58), are operated by electric power supplied from the power source section 70. So that the portability of the electronic cassette 10 is not adversely affected, the power source section 70 incorporates therein a battery (a chargeable secondary battery) and supplies electric power from the charged battery to the various types of circuits and elements. Note that illustration of the wires that connect the power source section 70 with the various types of circuits and respective elements is omitted from FIG. 9.

Operation of the electronic cassette 10 relating to the present exemplary embodiment is described next.

As shown in FIG. 1 and FIG. 3, the electronic cassette 10 is transported in the housed state in which the image capturing unit 12 and the control unit 14 are folded-up and superposed one on another.

On the other hand, when a radiographic image is to be captured, the electronic cassette 10 is set in the unfolded state in which the image capturing unit 12 and the control unit 14 are lined-up next to one another as shown in FIG. 2. Further, the electronic cassette 10 receives patient information from the console via the radio communication section 60. In response to the reception of the patient information, the cassette controller 58 displays, on the display section 19A, information (e.g., the name or ID of the patient) relating to the patient that is based on the received patient information. In this way, at the electronic cassette 10 relating to the present exemplary embodiment, because the name or ID is displayed on the display section 19A, the radiologic technician can reliably confirm whether or not there is mistaken identification of the patient on whom radiographic image capturing is about to be carried out, by, for example, the radiologic technician confirming the name with the patient himself/herself, and comparing the confirmed name with the name displayed on the screen.

When the electronic cassette 10 is in the housed state, capturing of still images can be carried out. When the electronic cassette 10 is in the unfolded state, capturing of video images can be carried out.

Figure 10:
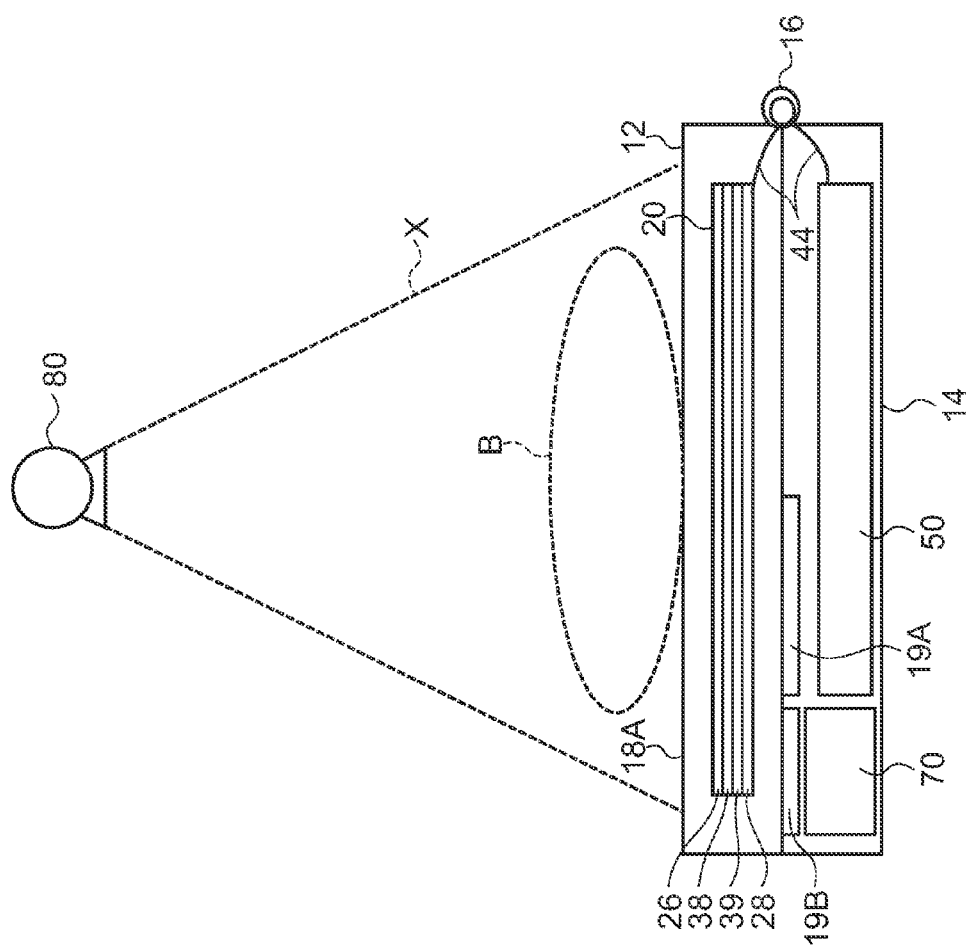
FIG. 10 is a sectional view showing the state of placement when carrying out image capturing at the electronic cassette in the housed state relating to the exemplary embodiment.
Figure 11:
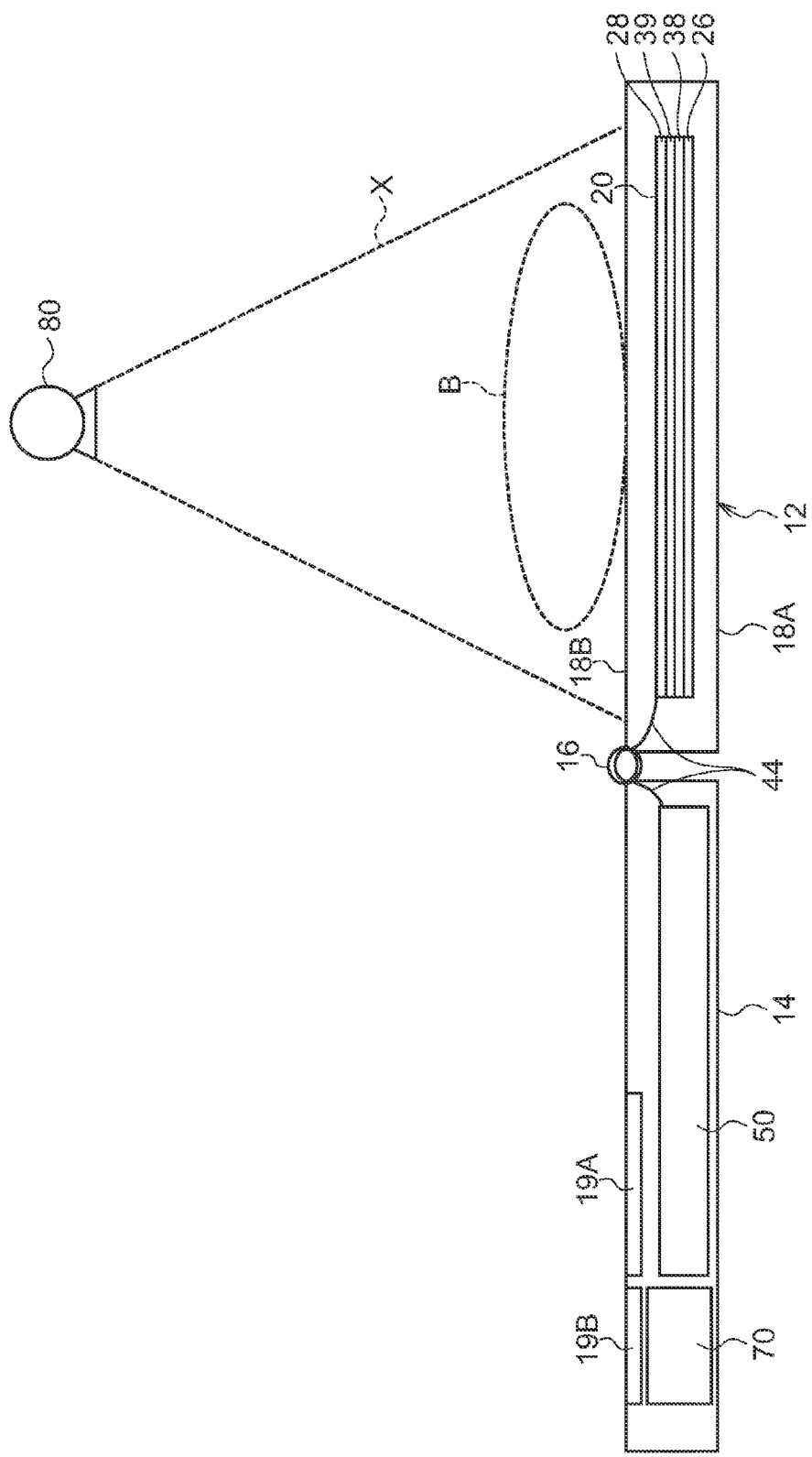
FIG. 11 is a sectional view showing the state of placement when carrying out image capturing at the electronic cassette in the unfolded state relating to the exemplary embodiment.

In a case in which the radiologic technician is to carry out capturing of a still image after completing confirmation of the patient's name, as shown in FIG. 10, the radiologic technician sets the electronic cassette 10 in the housed state and disposes the electronic cassette 10 such that there is an interval between the electronic cassette 10 and a radiation generating device 80 that generates radiation, and places region B that is the object of image capturing of the patient on the irradiated surface 18A. In a case of capturing video images, as shown in FIG. 11, the radiologic technician sets the electronic cassette 10 in the unfolded state and disposes the electronic cassette 10 such that there is an interval between the electronic cassette 10 and the radiation generating device 80, and places the region B that is the object of image capturing of the patient on the irradiated surface 18B.

On the basis of the results of detection of the opening/closing sensor 45, the cassette controller 58 grasps the opened/closed state of the image capturing unit 12 and the control unit 14. If the state is the housed state, the image capturing mode is a still image capturing mode in which capturing of still images is possible. If the state is the unfolded state, the image capturing mode is a video image capturing mode in which capturing of video images is possible. The cassette controller 58 gives notice of the image capturing mode to the console via the radio communication section 60.

At the console, setting of image capturing conditions that correspond to the notified image capturing mode becomes possible, and the image capturing conditions are set by the radiologic technician. After setting of the image capturing conditions is completed, the console transmits image capturing condition information, that expresses the set image capturing conditions, to the electronic cassette 10 by radio communication.

After setting of the image capturing conditions is completed, the radiologic technician carries out, at the console, an instructing operation that instructs the start of image capturing. Due thereto, radiation of a radiation amount that corresponds to the image capturing conditions or the like that were provided in advance, is emitted from the radiation generating device 80. Due to the radiation X emitted from the radiation generating device 80 passing through the region B that is the object of image capturing, the radiation X carries image information, and thereafter, is irradiated onto the electronic cassette 10.

The radiation X that is irradiated from the radiation generating device 80 passes through the region B that is the object of image capturing, and thereafter, reaches the electronic cassette 10. Due thereto, charges, that correspond to the radiation amount of the irradiated radiation X, are collected and accumulated in the respective charge collecting electrodes 34 of the radiation detector 20 that is incorporated within the electronic cassette 10.

The cassette controller 58 controls the gate line driver 52 such that ON signals are outputted from the gate line driver 52 to the respective gate lines 40 in order and line-by-line, and the respective switch elements 24 that are connected to the respective gate lines 40 are turned on in order and line-by-line. Due thereto, the charges that are accumulated in the respective charge collecting electrodes 34 flow-out in order and line-by-line to the respective data lines 42 as electric signals. The electric signals, that have flowed-out to the respective data lines 42, are inputted to the signal processing section 54, are converted into digital image information, and are stored in the image memory 56.

In the case of the still image capturing mode, after reading-out of the image information of one frame (one shot) is finished, the cassette controller 58 ends the reading-out of the image information, and transmits the image information that is stored in the image memory 56 to the console. In the case of the video image capturing mode, the cassette controller 58 transmits, to the console and at any time, the image information that is stored in the image memory 56 while repeatedly carrying out reading-out of the image information.

In this way, at the electronic cassette 10, at the time of carrying out video image capturing in which the amount of generated heat is large, by setting the electronic cassette 10 in the unfolded state and carrying out video image capturing, transmission of the heat, that is generated at the controller 50 within the control unit 14, to the radiation detector 20 within the image capturing unit 12 can be suppressed. Therefore, changes in the characteristics of the radiation detector 20 are suppressed, the image quality of the radiographic image that is captured is stable, and the durability of the radiation detector 20 improves. Further, the image capturing unit 12 contacts the patient at the time of capturing a radiographic image. Therefore, by suppressing the transmission of heat that is generated at the controller 50 to the image capturing unit 12, it is possible to prevent the surface temperature of the image capturing unit 12 from becoming too high and the patient from feeling uncomfortable. Moreover, because the radiation detector 20 is a layered structure and the coefficients of thermal expansion of the members structuring the respective layers are different, the occurrence of deformation or breakage due to heat, and the adhesive deteriorating and peeling due to temperature cycles, can be suppressed.

Further, by setting the electronic cassette 10 in the unfolded state, the surface area increases, and therefore, the heat dissipating effect improves. In a case of capturing video images in particular, the amount of heat that is generated is large, and therefore, making the surface area larger is preferable from the standpoint of heat dissipation. The heat dissipating effect may be further improved by forming the surface of the control unit 14 to have convex and concave shapes so as to increase the surface area. The convex and concave shapes may be any of wave shapes, semispherical shapes, or the like.

By carrying out still image capturing with the electronic cassette 10 in the housed state, radiation is irradiated onto the radiation detector 20 from the irradiated surface 18A that is the reverse side, and therefore, a radiographic image having high resolution can be obtained. Further, by carrying out video image capturing with the electronic cassette 10 in the unfolded state, radiation is irradiated onto the radiation detector 20 from the irradiated surface 18B that is the obverse side, and the sensitivity of the radiation detector 20 to radiation is high. Therefore, the amount of radiation that is irradiated at the time of video image capturing can be kept small, and the amount of exposure of the region that is the object of image capturing can be kept low.

When the electronic cassette 10 is in the unfolded state, the radio communication section 60 is provided within the control unit 14 that is apart from the patient. In the case of radio communication, the antenna is apart from the patient, and therefore, it is difficult for radio interference to occur.

Figure 12:
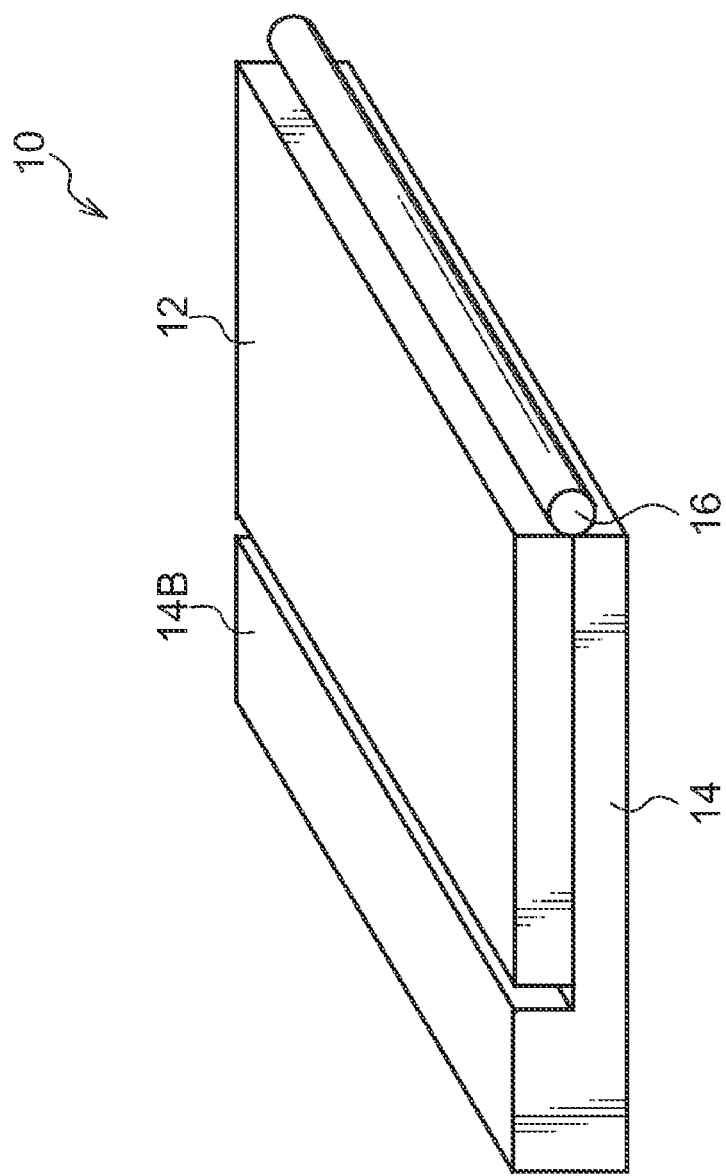
FIG. 12 is a perspective view showing the structure of the electronic cassette in the housed state relating to another exemplary embodiment.
Figure 13:
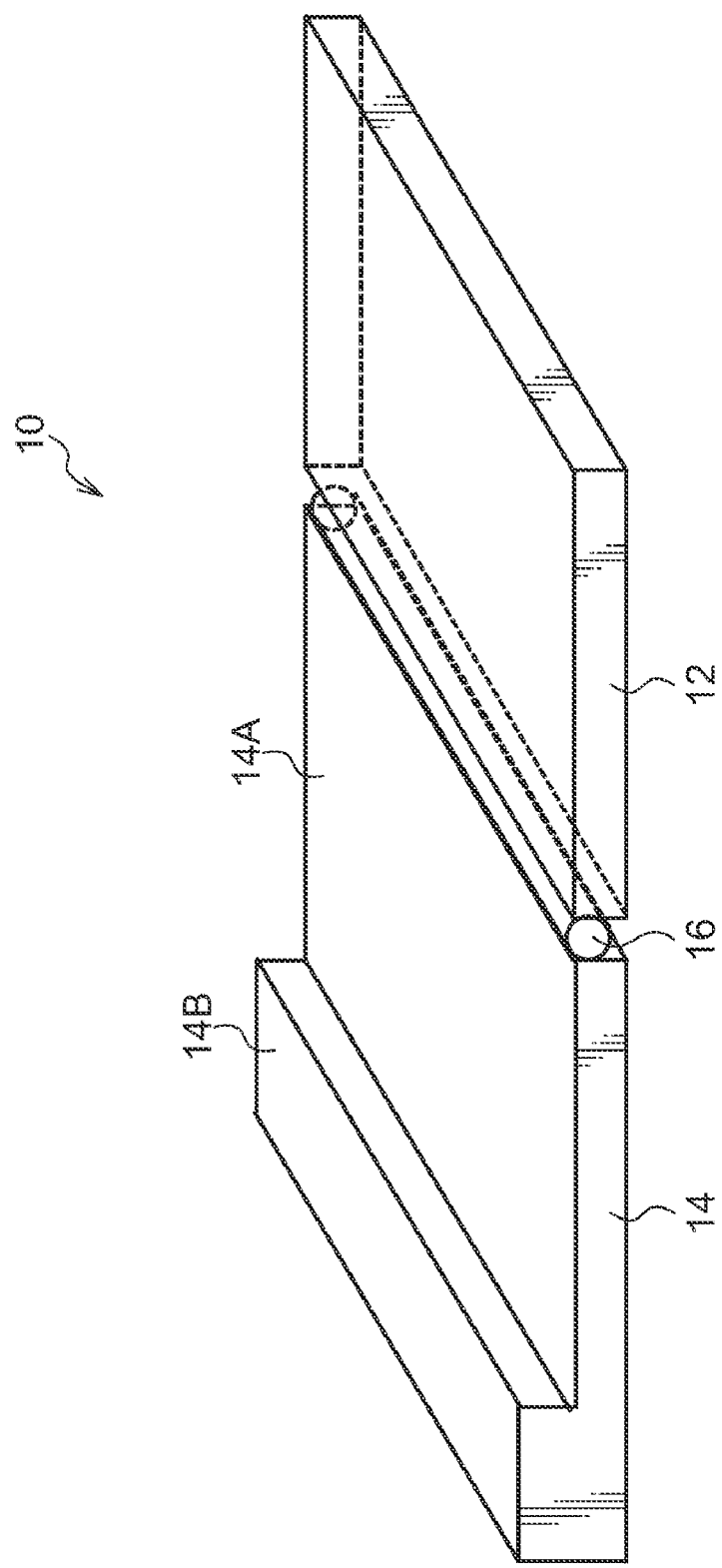
FIG. 13 is a perspective view showing the structure of the electronic cassette in the unfolded state relating to another exemplary embodiment.

Note that the above exemplary embodiment describes a case in which the image capturing unit 12 and the control unit 14 are formed to be the same height in order to eliminate a step between the image capturing unit 12 and the control unit 14 in the unfolded state (FIG. 2). However, the exemplary embodiment is not limited to the same. For example, in the same way as a liquid crystal display, the radiation detector 20 can be formed at a glass substrate and can be made to be relatively thin. At the controller 50, the circuits such as the inductors and the coils and the like are relatively thick, and, further, the battery and the like as well are relatively thick. Thus, as shown in FIG. 12 and FIG. 13, at the electronic cassette 10, the image capturing unit 12 may be formed to be thin, and the control unit 14 may be structured such that an overlapped portion 14A, on which the image capturing unit 12 is folded-up and superposed in the housed state, is formed to be thin and the same thickness as the image capturing unit 12, and a non-overlapped portion 14B, on which the image capturing unit 12 is not superposed, is formed to be thick, and circuits such as the inductors and coils and the like, as well as the battery, are disposed within the non-overlapped portion 14B. The display section 19A and the operation panel 19B may be provided at the overlapped portion 14A or may be provided at the non-overlapped portion 14B.

Although the above exemplary embodiment describes a case in which radio communication with an external device such as the console or the like is carried out, the exemplary embodiment is not limited to the same. For example, wired communication may be carried out. In this case as well, by providing a connector, to which is connected a cable for carrying out the wired communication, at the control unit 14, the connector and the cable do not bother the patient. Further, when placing the cassette under the subject, no frictional resistance or excessive load is applied, and it is therefore difficult for troubles with poor contact such as looseness or disconnection or the like to arise.

Further, although the present exemplary embodiment describes a case in which the image capturing mode is made to be the video image capturing mode when the electronic cassette 10 is set in the unfolded state, the exemplary embodiment is not limited to the same. For example, the electronic cassette 10 may be structured so as to accept an image capturing instruction for still image capturing from the operation panel 19B also when the electronic cassette 10 is in an unfolded state, and, in a case in which an image capturing instruction for still image capturing is accepted at the operation panel 19B, the cassette controller 58 may operate in the still image capturing mode also in the unfolded state.

Although the above exemplary embodiment describes a case in which information relating to the patient is displayed on the display section 19A, the exemplary embodiment is not limited to the same. For example, the captured radiographic image or the image capturing conditions may be displayed. Further, if the same region that is the object of image capturing of the patient is captured periodically and changes over time are observed, radiographic images that have been captured in the past at that region that is the object of image capturing of the patient may be received from the console and displayed. Moreover, a sample image or image capturing guidance may be displayed in accordance with the region that is the object of image capturing.

Figure 14:
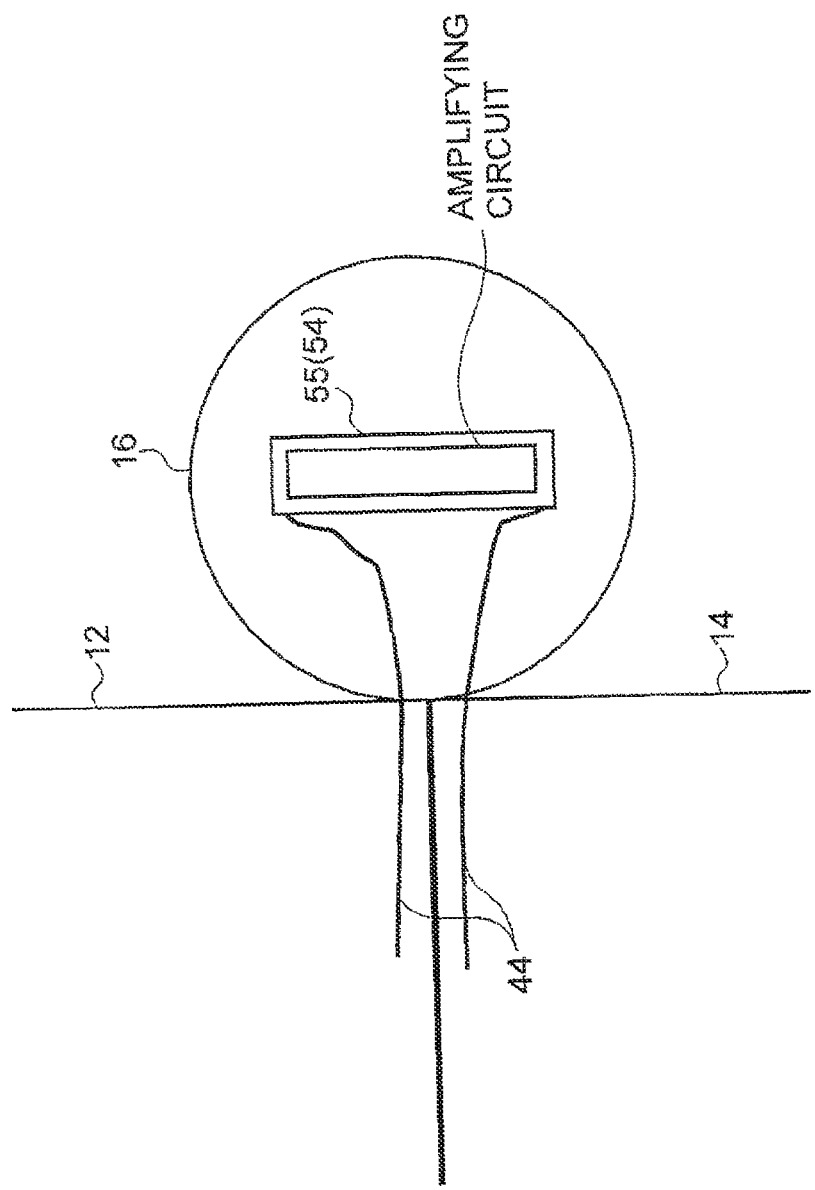
FIG. 14 is a sectional view showing a structure in which an integrated circuit is provided within the hinge relating to another exemplary embodiment.

The exemplary embodiment describes a case in which the gate line driver 52 and the signal processing section 54 are provided within the control unit 14, but the exemplary embodiment is not limited to the same. For example, the gate line driver 52 and/or the signal processing section 54 may be structured by an integrated circuit 55 such as an Application Specific Integrated Circuit (ASIC) or the like, and may be disposed within the hinge 16 as shown in FIG. 14. Due thereto, the effect of cooling the integrated circuit 55 can be improved. Note that the integrated circuit 55 does not necessarily have to be provided within the hinge 16, and may be provided in a vicinity of the hinge 16 as shown in FIG. 15.

Due to the electronic cassette 10 being opened and closed, the device state of the electronic cassette 10 may transition, such as the power source may be turned on and off, or the mode may shift from an inactive mode to an image capturing mode, or the like.

Further, the above respective exemplary embodiments describe cases in which the present invention is applied to the indirect-conversion-type radiation detector 20 that once converts radiation into light at the scintillator layer 28, and converts the converted light into charges at the photoconductive layers 30 and accumulates the charges. However, the exemplary embodiments are not limited to the same. For example, the present invention may be applied to a direct-conversion-type radiation detector that directly converts radiation into charges at sensor portions using amorphous selenium or the like, and accumulates the charges.

Figure 15:
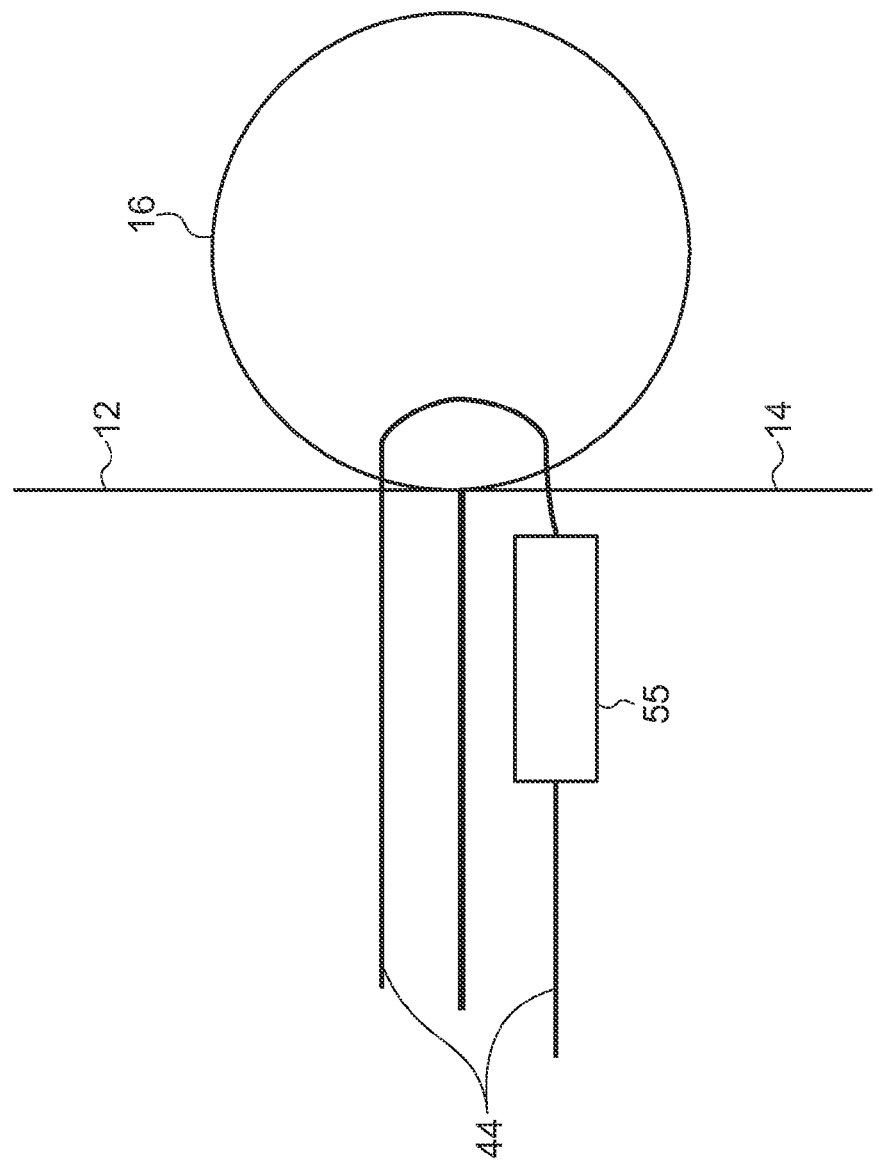
FIG. 15 is a sectional view showing a structure in which the integrated circuit is provided in a vicinity of the hinge relating to another exemplary embodiment.
Figure 16:
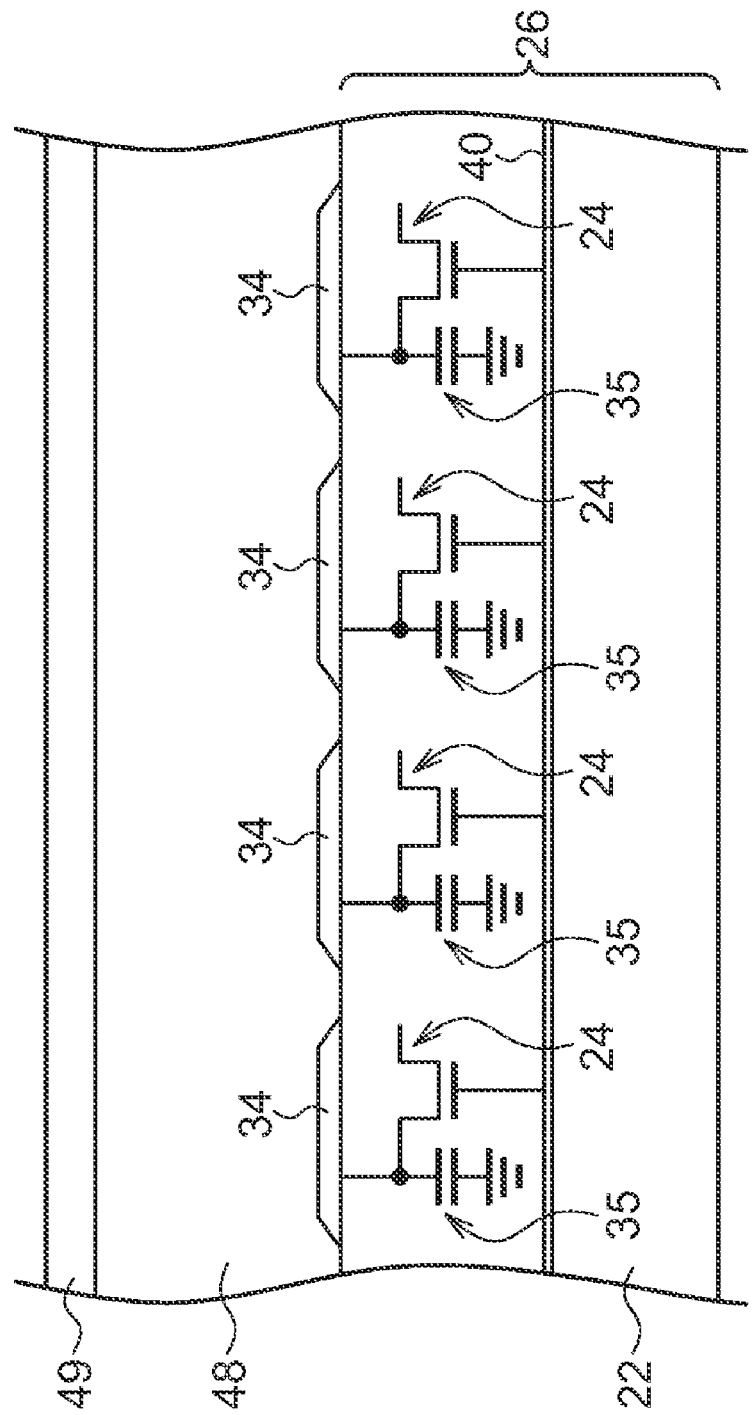
FIG. 16 is a sectional view schematically showing the structure of a direct-conversion-type radiation detector relating to another exemplary embodiment.

In a direct-conversion-type radiation detector, as shown in FIG. 15, a photoconductive layer 48 that converts incident radiation into charges is formed, as an example of a radiation conversion layer that converts incident radiation, on the TFT substrate 26.

Compounds whose main component is least one of amorphous Se, $Bi_{12}MO_{20}$ (M: Ti, Si, Ge), $Bi_4M_3O_{12}$ (M: Ti, Si, Ge), $Bi_2O_3$, $BiMO_4$ (M: Nb, Ta, V), $Bi_2WO_6$, $Bi_{24}B_2O_{39}$, ZnO, ZnS, ZnSe, ZnTe, $MNbO_3$ (M: Li, Na, K), PbO, $HgI_2$, $PbI_2$, CdS, CdSe, CdTe, $BiI_3$, GaAs or the like, or the like, are used as the photoconductive layer 48. Amorphous materials, that have high dark resistance, exhibit good photoconductivity with respect to X-ray irradiation, and at which large surface area growth at low temperatures by vacuum deposition is possible, are preferable.

A bias electrode 49, that is formed on the obverse side of the photoconductive layer 48 and is for applying bias voltage to the photoconductive layer 48, is formed on the photoconductive layer 48.

In the direct-conversion-type radiation detection device, in the same way as in the indirect-conversion-type radiation detection device, the charge collecting electrodes 34, that collect the charges generated at the photoconductive layer 48, are formed at the TFT substrate 26.

Further, the TFT substrate 26 in the direct-conversion-type radiation detection device has charge storage capacitors 35 that store the charges collected at the respective charge collecting electrodes 34. The charges stored in the respective charge storage capacitors 35 are read-out by the switch elements 24.

Moreover, the structures of the electronic cassette 10 and the radiation detector 20 that were described in the above exemplary embodiments are examples, and appropriate changes may, of course, be made within a range that does not deviate from the gist of the present invention.

What is claimed is:

1. A portable radiographic image capturing device comprising:
    an image capturing unit that is formed in the shape of a flat plate, and captures a radiographic image expressed by irradiated radiation, and comprises a radiation detector that outputs electric signals expressing a captured radiographic image, the image capturing unit being able to capture a radiographic image by radiation irradiated from either an obverse side or a reverse side of the flat plate;
    a control unit comprising a controller that controls image capturing operations of the radiation detector;
    a connecting member that connects the image capturing unit and the control unit such that the image capturing unit and the control unit can be opened and closed between an unfolded state, in which the image capturing unit and the control unit are lined-up next to one another, and a housed state, in which the image capturing unit and the control unit are folded-up so as to be superposed one on another; and
    a detecting section that detects an opened/closed state of the image capturing unit and the control unit,
    wherein, on the basis of results of detection by the detecting section, the controller controls the portable radiographic image capturing device to carry out still image capturing if the opened/closed state of the image capturing unit and the control unit is the housed state, and controls the portable radiographic image capturing device to carry out video image capturing if the opened/closed state is the unfolded state.

2. The portable radiographic image capturing device of claim 1, further comprising an accepting section that accepts an image capturing instruction for still image capturing also if the opened/closed state of the image capturing unit and the control unit is the unfolded state,
    wherein, if the accepting section accepts an image capturing instruction for still image capturing, the controller controls the portable radiographic image capturing device to carry out still image capturing also in the unfolded state.

3. The portable radiographic image capturing device of claim 1, wherein, at the radiation detector, a charge generating layer, at which charges are generated due to radiation being irradiated, and a substrate, that accumulates the charges generated at the charge generating layer and at which are formed switch elements for reading-out the charges, are layered, and the radiation detector is incorporated within the image capturing unit such that, in the housed state, the charge generating layer is at a side that opposes the control unit.

4. The portable radiographic image capturing device of claim 3, wherein the radiation detector comprises a substrate and a conversion layer that converts radiation irradiated onto the substrate into light, and the charges are generated at the charge generating layer due to the light converted from the radiation at the conversion layer.

5. The portable radiographic image capturing device of claim 4, wherein the charge generating layer comprises an organic photoelectric conversion material.

6. The portable radiographic image capturing device of claim 1, wherein the radiation detector is formed at a substrate that comprises plastic resin, aramid, bio-nanofibers, or flexible glass.

7. The portable radiographic image capturing device of claim 1, wherein the connecting member comprises therein an amplifying circuit that amplifies the electric signals outputted from the radiation detector.

8. The portable radiographic image capturing device of claim 1, wherein the control unit includes a radio communication section that carries out radio communication with an external device.

9. The portable radiographic image capturing device of claim 1, wherein a surface of the control unit is formed to have convex and concave shapes.

10. The portable radiographic image capturing device of claim 1, wherein the control unit has a display section at a surface that opposes the image capturing unit in the housed state.

* * * * *